(12) United States Patent
Peyman et al.

(10) Patent No.: US 7,828,440 B2
(45) Date of Patent: Nov. 9, 2010

(54) METHOD OF DETECTING GLAUCOMA

(76) Inventors: Gholam A. Peyman, 10650 W. Tropicana Cir., Sun City, AZ (US) 85351; Shin Yeneya, 3-60-8 Kamikoide Macbashi, Gunma (JP) 371-0037

( * ) Notice: Subject to any disclaimer, the term of this patent is extended or adjusted under 35 U.S.C. 154(b) by 0 days.

(21) Appl. No.: 12/453,657

(22) Filed: May 18, 2009

(65) Prior Publication Data

US 2009/0227891 A1   Sep. 10, 2009

Related U.S. Application Data

(63) Continuation-in-part of application No. 11/840,675, filed on Aug. 17, 2007, now Pat. No. 7,549,752.

(51) Int. Cl.
*A61B 3/00* (2006.01)
*A61B 3/02* (2006.01)

(52) U.S. Cl. .................................... 351/246; 351/239

(58) Field of Classification Search .......... 351/200–246
See application file for complete search history.

(56) References Cited

U.S. PATENT DOCUMENTS

| | | | | |
|---|---|---|---|---|
| 5,784,162 | A | * | 7/1998 | Cabib et al. .................. 356/456 |
| 6,276,798 | B1 | | 8/2001 | Gil et al. ...................... 351/206 |
| 6,419,361 | B2 | | 7/2002 | Cabib et al. .................. 351/205 |
| 6,494,578 | B1 | * | 12/2002 | Plummer et al. ............. 351/224 |

* cited by examiner

*Primary Examiner*—Mohammed Hasan
(74) *Attorney, Agent, or Firm*—Wenderoth, Lind & Ponack, L.L.P.

(57) ABSTRACT

A method of testing for an ocular disease in an eye includes measuring a condition of the eye to receive a first value, placing an instrument adjacent the surface of the eye, changing the pressure in the eye using the instrument after measuring the condition, measuring the condition of the eye, after changing the pressure, to receive a second value, and comparing the first value to the second value.

13 Claims, 8 Drawing Sheets

METHOD OF DETECTING GLAUCOMA

This application is a continuation-in-part of application Ser. No. 11/840,675, filed Aug. 17, 2007 now U.S. Pat. No. 7,549,752 entitled "Method of Glaucoma Detection", the entire contents of which are herein incorporated by reference.

BACKGROUND OF THE INVENTION

Progressive optic atrophy associated with excavation of optic nerve head is a hallmark of glaucoma that leads to visual field defects. Although increased intraocular pressure is an obvious risk factor, the mechanisms that lead to the damage of the optic nerve head is still a controversial issue, because glaucomatous optic nerve damage may develop at any level of intraocular pressure. In the past Circulatory or vascular alterations have been considered as a risk factor accounting for the development of glaucomatous optic nerve damage. Fluorescein angiography (FAG) has shown filling defects in the optic disc of eyes with NTG. Color Doppler imaging (CDI) has demonstrated an increase in resistive index (RI) of the ophthalmic arteries in eyes with glaucoma. Laser Doppler analysis showed a decrease in retinal and optic nerve flow in glaucoma patients. Further, measurements of pulsatile ocular blood flow (POBF) showed the POBF to be significantly lower in NTG eyes with or without field loss than in normal subjects.

SUMMARY OF THE INVENTION

The present invention relates to a method, including the steps of mapping at least a portion of the fundus of the eye by forming a plurality of pixels, estimating the oxygen saturation level at each of the plurality of pixels, superimposing the fundus maps on maps of anatomic borderlines, and comparing portions of the superimposed fundus maps to predetermined fundus maps.

The present invention also relates to a method, including the steps of mapping at least a portion of the fundus of the eye by forming a plurality of pixels using light from a spectral image system, dividing each light beam from the light that is reflected from the fundus with an interferometer into two coherent beams, recombining the two coherent beams and detecting the interference, measuring the interference as a function of the optical path difference, comparing the intensity of the light to the optical path difference for each of the plurality of pixels, estimating the oxygen saturation level at each of the plurality of pixels, superimposing the fundus maps on maps of anatomic borderlines and comparing portions of the superimposed fundus maps to predetermined fundus maps.

Additional features and advantages are described herein, and will be apparent from, the following Detailed Description and the figures.

BRIEF DESCRIPTION OF THE FIGURES

FIG. 2 illustrates a map of the area of HFA used to calculate the mean of the total deviation (TD);

DETAILED DESCRIPTION OF THE INVENTION

The present invention relates to a method in which the oxygen saturation (OS) levels in the fundus can be estimated non-invasively at each pixel with about 35 degrees to about 100 degrees (or any other suitable amount) of fundus view. The method can be used on patients with central retinal vein occlusion to evaluate the level of ischemia in the fundus. The oxygen saturation (OS) levels are measured quantitatively in the retina near the optic disc including the area corresponding to the arcuate retinal nerve fiber in eyes with open-angle glaucoma (OAG).

The oxygen saturation images can be obtained by spectral image (SRI) system. Generally, an SRI system instrument consists of a SD-200 optical head, which uses a Sagnac interferometer mounted on top of a fundus camera (TRC-50IA; Topcon Co., Tokyo, Japan) and a software module consisting of an acquisition and an analysis module; however the SRI system can be any suitable system. Generally, the SRI system allows the measurement of a spectrum in each pixel of the fundus image.

Preferably, after obtaining complete mydriasis with instillation of 0.5% tropicamide and 0.5% phenylephrine hydrochloride, the fundus is scanned by the camera for about 100 milliseconds to about 6 seconds using light between 480 and 600 nm; however, it is noted that these parameters are merely exemplary and can be any suitable parameters. Every light beam reflected from the fundus can be divided by the Sagnac interferometer into two coherent beams, which can be recombined and the interference detected. The interference can then be measured by a detector as a function of the optical path difference. The intensity versus optical path difference function, called an interferogram, can be Fourier-transformed to achieve the spectral wave, which can be carried out for every pixel of the image.

Figure 1:
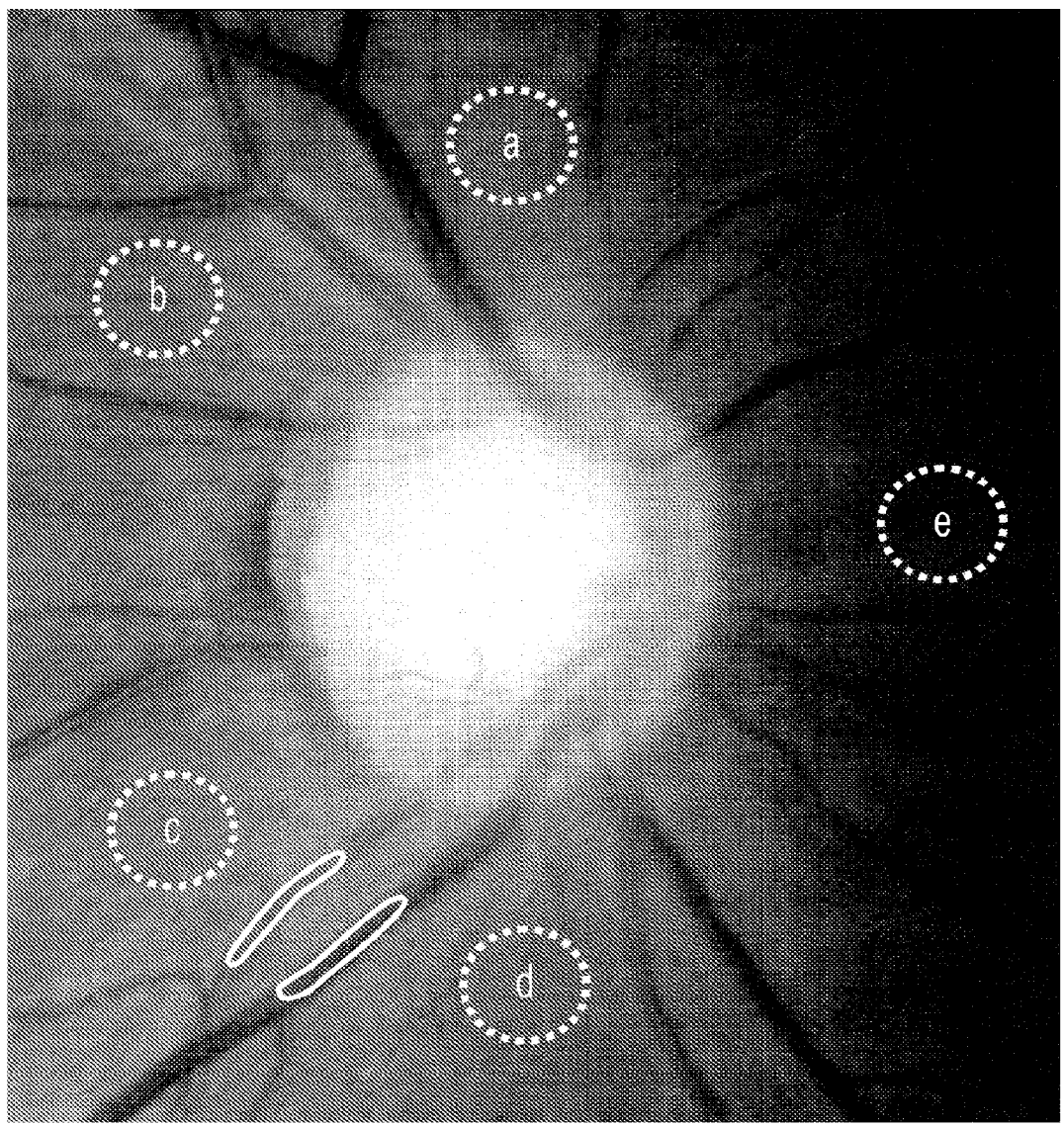
FIG. 1 illustrates an image of a fundus showing seven areas where oxygen saturation (OS) level were measured.

To estimate oxygen saturation level from the spectrum in each pixel, the applicability of Beer-Lambert law can be assumed by constructing a mathematical model to describe the measured fundus layers. For example, standard extinction coefficients of oxygenated and deoxygenated hemoglobin (FIG. 1a) and direct response in the system can be substituted by a model based on Beer-Lambert, in which the oxygen saturation and blood column thickness are free parameters. These parameters can be then estimated to obtain the best fit between the model and the actual measured spectrum (FIG. 1b), yielding the oxygen saturation estimate for each pixel of the map. This transformation can be carried out in every pixel to get an image map of the fundus in about 35 degrees to about 100 degrees or any other suitable amount.

The oxygen saturation maps can then be superimposed on maps of anatomic borderlines by a separate analysis to serve as a guide and as a spatial coordinating system. This can provide geographic maps, and the oxygen saturation pictures with which many physicians are familiar. Acquisition time with a spectral resolution of about 15 nm at about 500 nm can be at about 100 milliseconds to about 6 seconds for a 284×244 pixel image; however, it is noted that these parameters are merely exemplary and can be any suitable parameters. Using this technique and by applying different colors to different oxygen saturation level, red (e.g., about 100%) to purple (e.g., about 40%), the fundus can represent two dimensionally. Coefficient variation of images taken with SRI system can be examined and may be within 5%.

Using geographic maps, seven different points on the retina can be analyzed, including retinal vessels to compare the values among low tension and high tension subgroups and normal groups or any other suitable groups. If desired, five juxta-papillary points (e.g., superior, superotemporal, inferotemporal, inferior, and nasal point) with approximately 200.mu.m in diameter, avoiding the visible vessels in the retina, and 200.mu.m in length along both retinal artery and the vein at 0.75 disc-diameter from the disc margin can be measured. However, it is noted that any number of juxta-papillary points can be measured having any desired and/or suitable dimensions.

Figure 2:
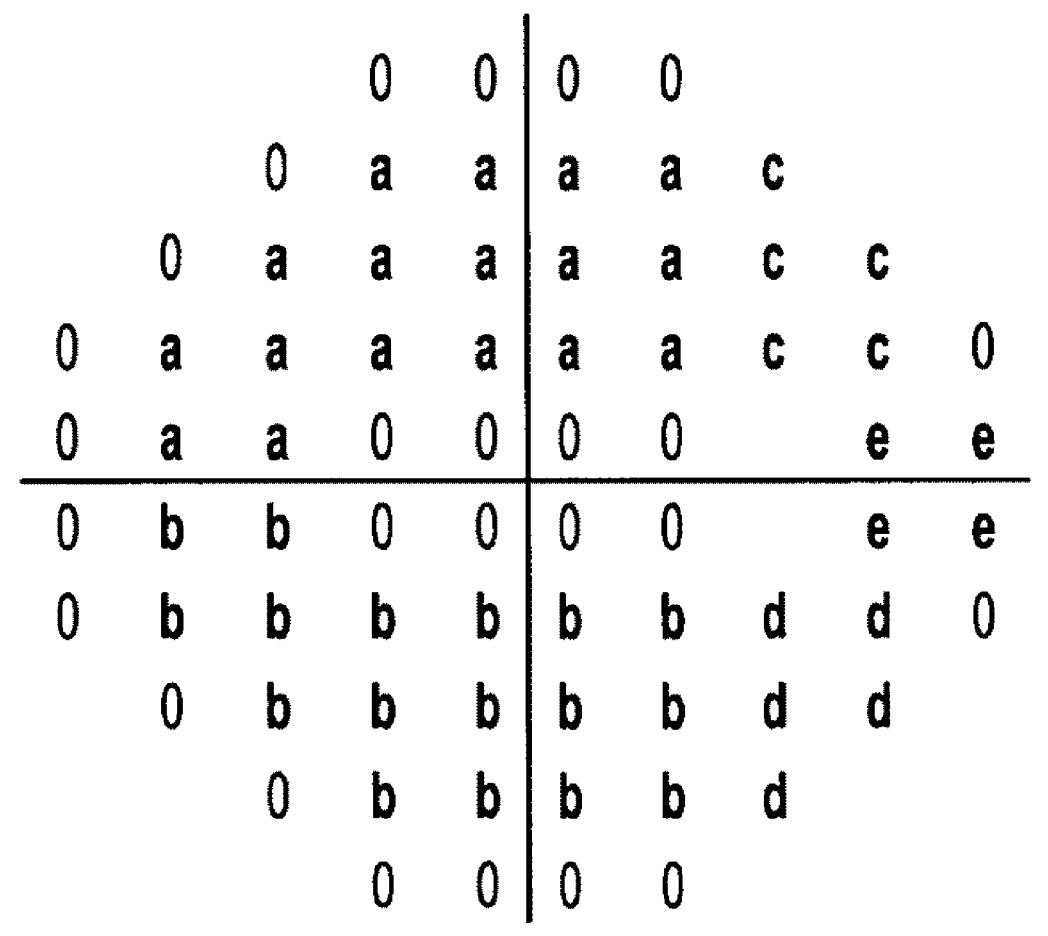

The mean total deviation (TD) of oxygen saturation values can also be calculated at 17 points each in the upper and the lower arcuate area (FIGS. 2a and b), 5 points upper and lower to the blind spot (FIGS. 2c and d), and 4 points temporal to the blind spot related to the optic disc (FIG. 2e). These five regional TD values can correlate the oxygen saturation value at five measurement points respectively. Please note that any number of points each in the upper and the lower arcuate area can be used and in any areas desired.

Oxygen saturation measurement using a Fourier-transform-based SRI system can show the oxygen saturation level to be significantly lower in OAG eyes compared with normal eyes. In low tension subgroups, decreased oxygen saturation levels in the juxta-papillary area can be evident and can be observed in 3 measurement points (superior, nasal and inferotemporal point) out of five points, while the oxygen saturation level at only inferotemporal point can be significantly low in high tension subgroups.

Generally, there is no difference between the low tension and the high tensions subgroups by means of several HFA calculations, thus the severity of these two groups' glaucoma can be estimated to be about the same. Nevertheless, there can be a difference in oxygen saturation levels between the two subgroups, although the oxygen saturation level in the retinal artery, vein, and the difference between them in all the groups may be the same. The decreased oxygen saturation level in relationship with the retinal function may be related to development of glaucoma especially in normal tension glaucoma (NTG).

Patients with NTG have vasospastic episodes, often disc hemorrhages and peripapillary chorioretinal atrophy. In addition, higher endothelin-1 plasma levels in NTG patients than high-tension glaucoma patients have been reported. Decreased OS level in the juxta-papillary area may be present in NTG patients even before the visual field-loss becomes evident.

In the high tension group, oxygen saturation level can be significantly decreased at the inferotemporal point compared to normal subjects. Among 5 juxta-papillary measurement points, the oxygen saturation levels at inferotemporal, superotemporal, and inferior points were lower than those at nasal point. Averaged oxygen saturation value at inferotemporal and superotemporal points can be significantly correlated with the mean deviation. Additionally, the TD in the upper arcuate area (relating to inferotemporal point), may show good correlation with low oxygen saturation level at corresponding juxta-papillary area with a statistical significance. The decreased oxygen saturation levels at peri-papillary area may have resulted in decreased retinal sensitivity in HVF, in the high tension and in NTG patients.

Different oxygen saturation levels in the peripapillary area may be observed among low tension, high tension and normal eyes and also altered relation between the oxygen saturation level and HVF analysis in low tension and high tension glaucoma patients. Oxygen saturation measurement can be also a useful method in evaluation and potentially management of OAG patients.

Figure 8:
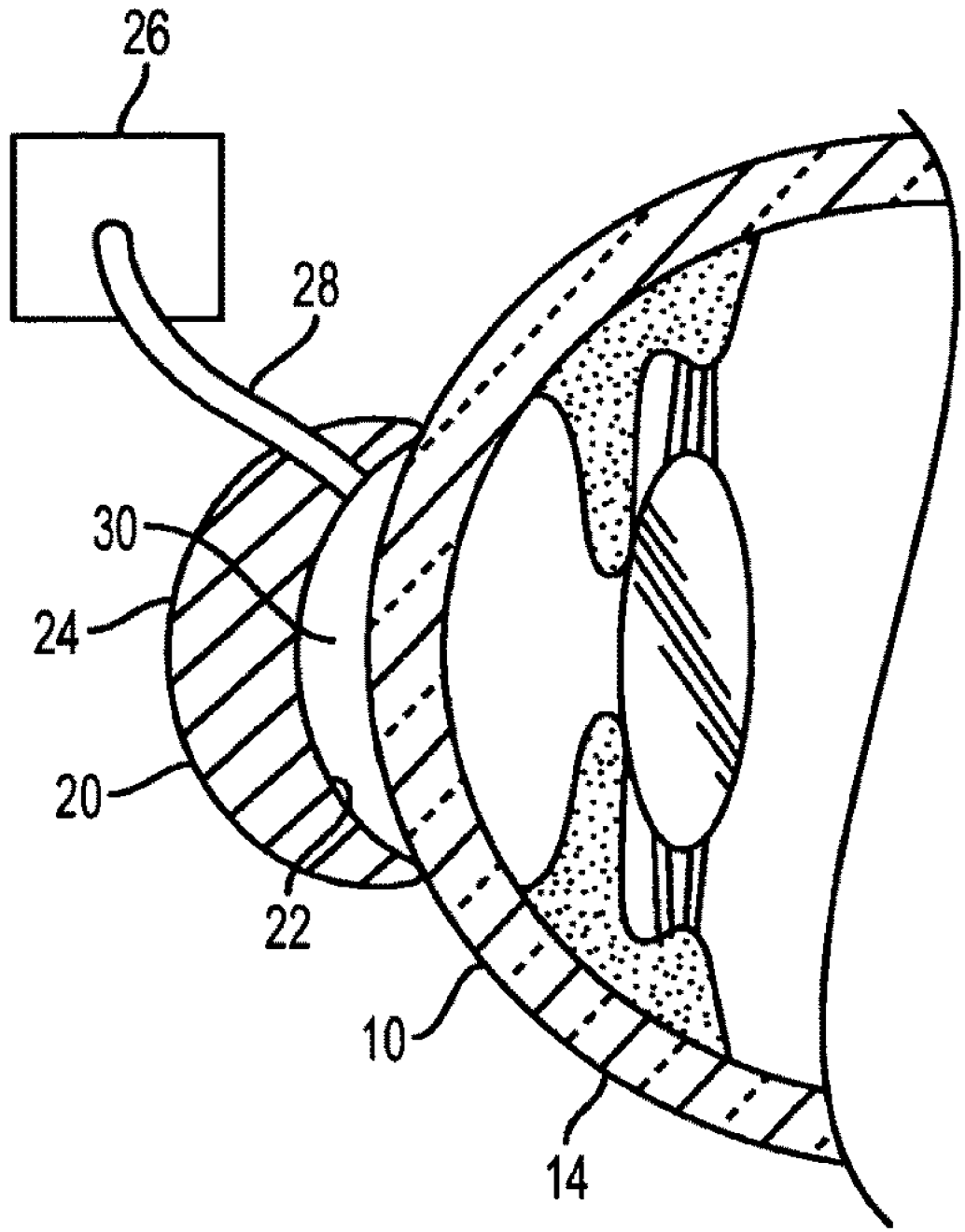
FIG. 8 is a side elevational view in section of a device that creates pressure in the eye positioned adjacent the external surface of the eye.

FIG. 8 illustrates another embodiment in which glaucoma can be detected using a device 20 and method that increases pressure in the eye 10. The device 20 can increase pressure by creating suction and/or a vacuum at a portion on the eye. For example, the device can be positioned at or near the cornea and/or the sclera or at any other suitable position on the eye. Additionally, if desired, the device can apply pressure to the eye, thus increasing the pressure.

The device to increase the pressure can be substantially circular with an arcuate inner surface 22 and an outer surface 24. That is, the surface that is positioned adjacent the cornea and/or sclera can have an arcuate surface or any other suitable surface. The radius of curvature of the arcuate surface can be about the same as the curvature of the eye or have a steeper or shallower radius of curvature of the eye. The device can be formed of any suitable material and be formed from transparent, translucent or opaque material.

To apply the vacuum, a pump 26 can be attached or coupled to the device use a tube 28 or any other suitable means. The pump through tubing can create suction within the space 30 between the device and the eye, thereby creating a vacuum. This vacuum will increase the pressure in the eye.

A similarly shaped device can be used to increase the pressure in the eye by applying pressure to the external surface 24 of the device.

It is noted that any suitable device to increase pressure can be used in this procedure.

Preferably, the pressure in the eye is gradually raised to between about 1 mm Hg to about 30 mm Hg, and more preferably to between about 3 mm Hg to about 10 mm Hg or to any specific pressure within or without of these ranges or any suitable range therein. For example, the pressure can be raised to 6 mm Hg, if desired or any pressure outside of the above stated range, if suitable. The pressure is maintained at the desired amount for a predetermined time. For example, the pressure can be maintained for about 5 to about 10 seconds or up to about 1 minute, or any other specific suitable time or range of times. Before, during and after the increase in pressure, the oxygen saturation levels are measured and compared and/or contrasted to a normal eye or any other determined amount.

If desired, the pressure can be reduced and the oxygen saturation levels can be monitored to determine the length of time that is required for the levels to return to normal or substantially normal level. This type of stress test will indicate whether a patient has glaucoma.

The difference between oxymetry values (i.e., oxygen saturation levels) in sitting vs. laying down position can also be indicative of glaucoma.

EXAMPLES

The oxygen saturation level of each point was masked as to the subjects' characteristics. Unpaired t-test or non-repeated measures of ANOVA followed by Bonferroni correction or repeated measures of ANOVA followed by Student-Newman-Keuls test was used for statistical evaluation.

Fifty-six eyes of 56 Japanese OAG patients and 20 eyes of 20 normal Japanese were recruited for the study. Among 56 OAG eyes, 15 eyes (15 patients) constantly showed recorded intraocular pressure (IOP) of .ltoreq. 15 mmHg and were classified as low-tension (LT) subgroup. The other 41 eyes from 41 patients showed recorded IOP of .gtoreq.22 mmHg in multiple readings and were classified as high-tension (HT) subgroup, during more than 6 of months follow-up. The subjects age were 27 to 73 (mean .+-.SD, 60.5.+-0.11.9) years in the LT subgroup, 22 to 78 (55.9.+-0.14.8) years in the HT subgroup, and 31 to 79 (52.6.+-0.15.7) years in the normal group. The differences in the mean ages among the three groups were not statistically significant ($p>0.05$, non-repeated measures of ANOVA).

All patients underwent routine ophthalmic examination previous to this study. There was no obvious change in normal group except for mild senile cataract and refractive error. Patients who had a history of systemic diseases such as systemic hypertension or diabetes mellitus were excluded from this study. Additionally, all LT patients were examined by CT scan or by magnetic resonance images (MRI) that showed normal results. This study was carried out with approval from the review board of the institute and informed written consent was obtained from all the patients. All but two patients had never taken any instillation of medication to lower the IOP, and those who had been taking it were withheld from it for at least 4 weeks before entry in this study. All OAG patients had visual field examination with automatic static perimetry at least twice that showed characteristic glaucoma visual field losses in all. A Humphrey field analysis (HFA) with the program 30-2 SITA (Zeiss Humphrey Instruments, Dublin, Calif., USA) was performed. The oxygen saturation (OS) level in the fundus was measured with Fourier-transform-based spectral retinal image (SRI) system (Retinal Cube; ASI Co. Migdal Hemak, Israel) around noon till 3 o'clock in the afternoon.

Results

The intraocular Pressure (IOP) of all subjects was measured using a Goldmann applanation tonomer (Haag-Streit, Berne, Switzerland) just before the OS level measurement. It averaged 12.9.+-0.1.4 mmHg in the LT subgroup, 20.0.+-0.4.1 mmHg in the HT subgroup, and 14.0.+-0.2.8 mmHg in the normal group. The differences among the HT subgroup and the other two were statistically significant ($p<0.001$).

The average of the mean deviation (MD) of the light intensity was −8.4.+-0.6.5 dB in the LT subgroup and −7.7.+-0.6.9 dB in the HT subgroup. The mean of total deviation (TD) of 17 points in the upper arcuate and in the lower arcuate area respectively, that of 5 points upper to the blind spot, that of 5 points lower to the blind spot, and that of 4 points temporal to the blind spot was −9.9.+-0.9.−7.5.+-0.6., −6.5.+-0.7., −6.4.+-0.8., and −4.7.+-0.7. dB in the LT subgroup and −7.9.+-0.9.0, −8.6.+-0.8.−4.0.+-0.6., −4.7.+-0.5., and −3.4.+-0.6. dB in the HT subgroup, respectively. All of these HFA results showed no significant difference between the two OAG subgroups (unpaired t-test).

Figure 3:
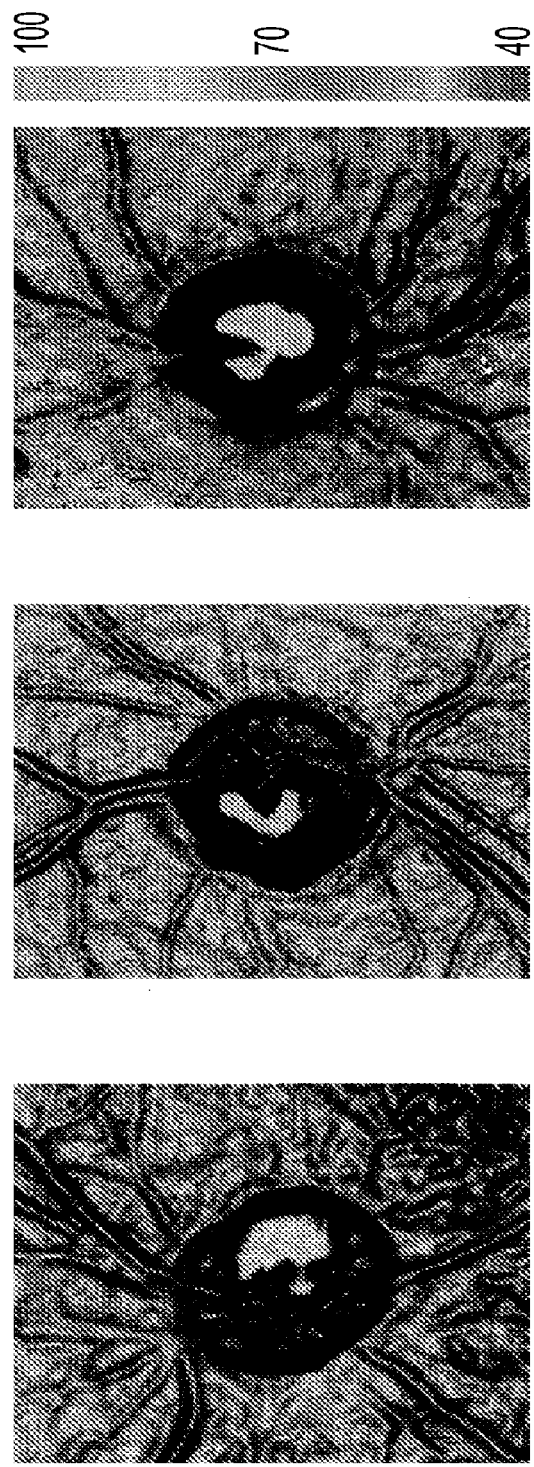
FIG. 3 illustrates oxygen saturation image maps.
Figure 4:
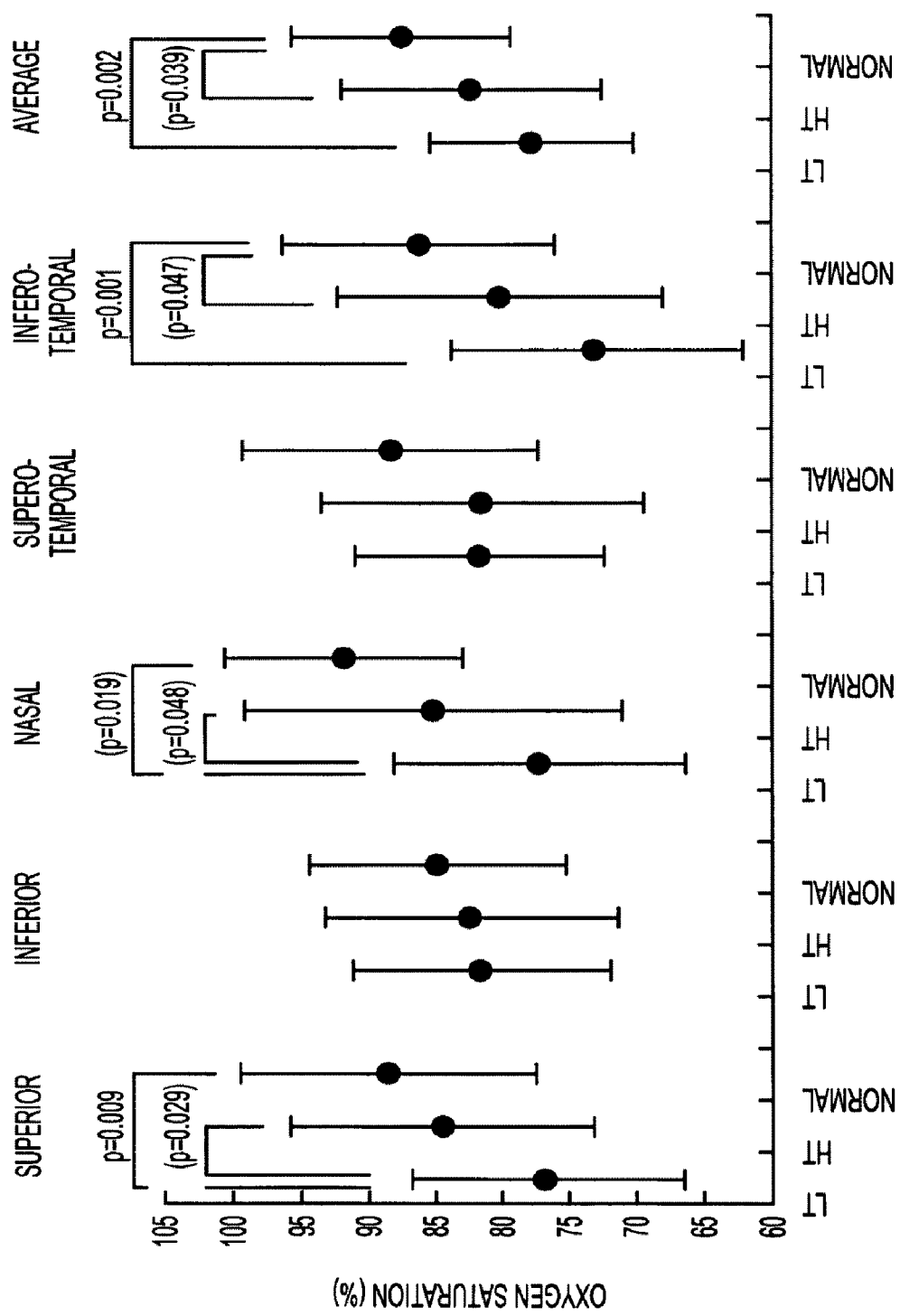
FIG. 4 illustrates a comparison of the oxygen saturation levels at the superior, inferior, nasal, superotemporal, inferotemporal juxta-papillary points, and the average of these five points among three groups.

In the normal eyes, OS map demonstrated dominantly yellow to red, with a few green color dots surrounding the optic disc (FIG. 3a) that suggested OS levels of the retina at corresponding area were higher than 80%. In contrast, green and/or blue dots overriding in OS maps of the LT subgroup implied OS levels in the retina to be approximated approximately from 70% to 80% (FIG. 3c). Whereas OS levels in the HT subgroup were more variable than in the LT subgroup, averaged color range lay in the middle of the normal group and the LT subgroup in most of eyes (FIG. 3b). The edge of vessels and rim of the disc were artificially delineated to make them clearer. OS levels in the retina at 5 points in the juxta-papillary retina, as well as in both the retinal artery and vein, were summarized in Table 1 and FIG. 4.

OS levels of both the LT and the HT subgroups were significantly lower than those of the normal group at the inferotemporal point and than the averaged OS value of the juxta-papillary five points (p=0.047.about.0.001). At the superior and nasal points, OS level of the LT subgroup showed significant decreases as compared with the HT subgroup (p=0.026 and 0.048 respectively) and also those of the normal group (p=0.009 and 0.019 respectively). Except the inferior and the superotemporal points, the OS levels at juxta-papillary area of both HT and LT subgroups were lower than those of normal subjects.

OS levels in the retinal artery and vein showed no significant differences among these three groups. The value of OS level reduction between artery and vein (artery-vein) also showed no significant inter-group difference (Table 1).

Figure 5:
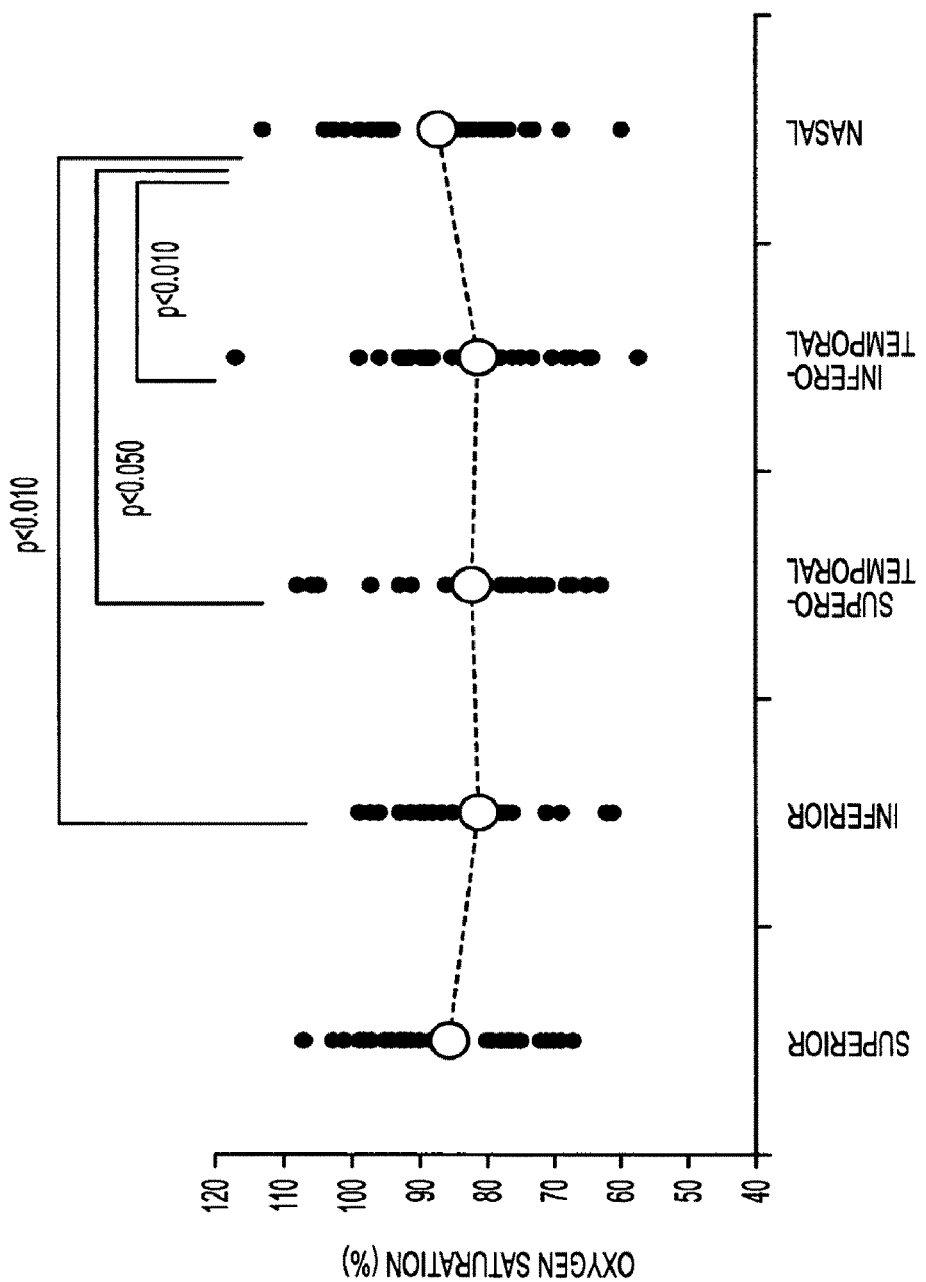
FIG. 5 illustrates oxygen saturation levels at 5 juxta-papillary points of a high tension subgroup.

Differences of OS levels among the 5 juxta-papillary points were then examined. There were no statistically significant differences in the normal group and the LT subgroup. On the other hand, in the HT subgroup, inferior, superotemporal, and inferotemporal points were significantly lower as compared with nasal point (<0.010, p<0.050, p<0.010, respectively; FIG. 5).

Figure 6:
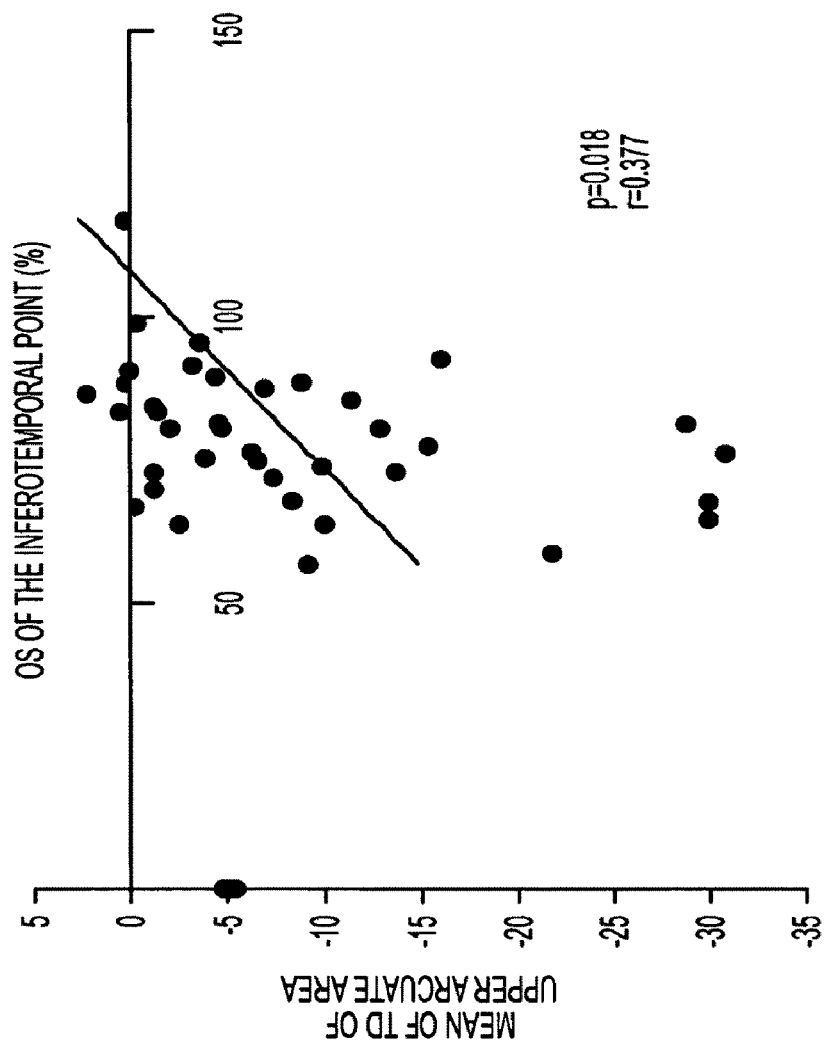
FIG. 6 illustrates correlation between the mean of TD of the 17 points in the upper arcuate area and the oxygen saturation value at the inferotemporal point of the high tension subgroup.
Figure 7:
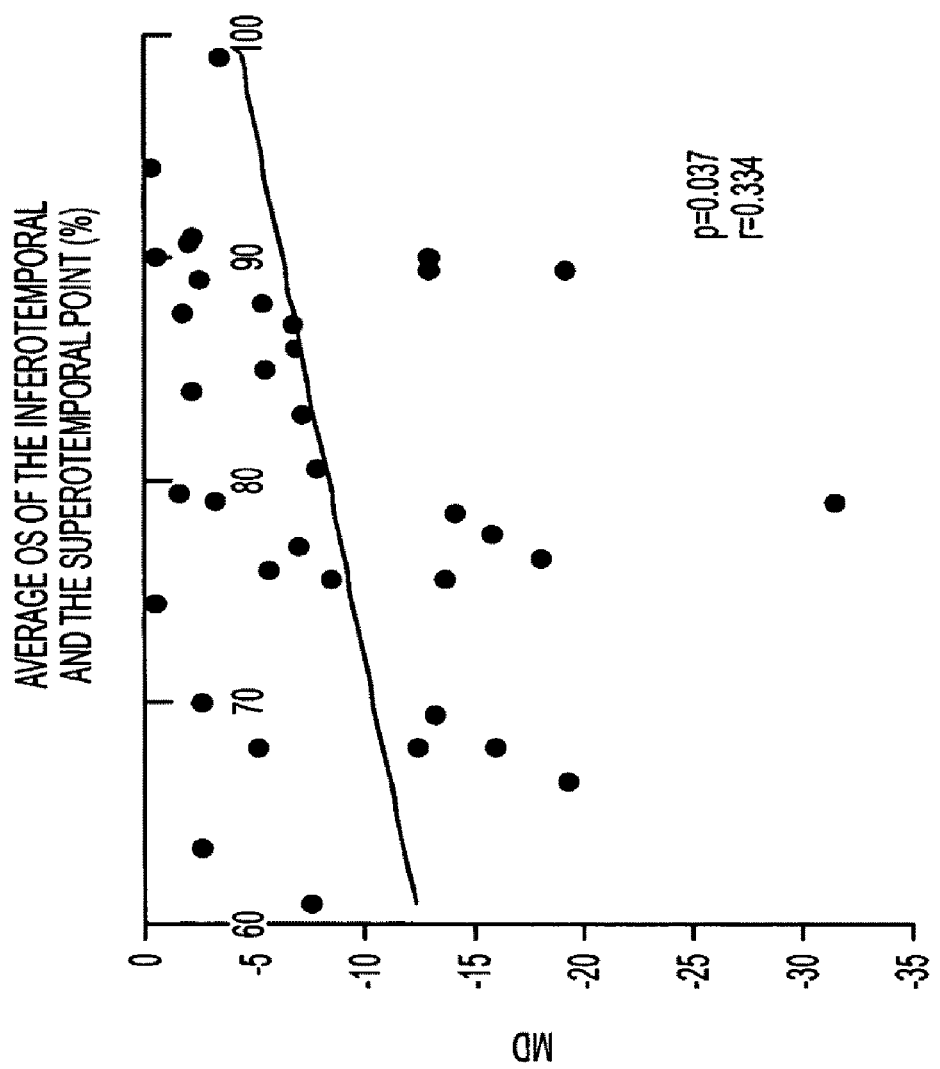
FIG. 7 illustrates a correlation between MD and the averaged oxygen saturation value at the inferotemporal and the suprerotemporal points of the high tension subgroup.

There was a statistically significant correlation between the mean of TD of the 17 points in the upper arcuate area and the OS level of the inferotemporal point (p=0.018, r=0.377; FIG. 6, table 2) in the HT subgroup. The correlation between MD and the averaged OS value of the inferotemporal and the superotemporal point was also statistically significant (p=0.037, r=0.334; FIG. 7). No significant correlation was observed between MD and the averaged OS value of the 5 juxta-papillary points, or between the mean of TD of 17 points in the lower arcuate area and the OS level at the superotemporal point. In the LT subgroup, no such correlation was present (Table 2).

TABLE 1

|  | Normal | LT | HT |
|---|---|---|---|
| Superior | 88.5 ± 11.1 | 76.6 ± 10.2 | 84.4 ± 11.4 |
| Inferior | 84.8 ± 9.6 | 81.5 ± 9.7 | 82.3 ± 11.0 |
| Nasal | 91.8 ± 8.9 | 77.2 ± 11.0 | 85.1 ± 14.1 |
| Superotemp. | 88.4 ± 11.1 | 81.7 ± 9.4 | 81.5 ± 12.1 |
| Inferotemp. | 86.3 ± 10.2 | 73.0 ± 10.9 | 80.2 ± 12.1 |
| Average | 87.6 ± 8.2 | 77.8 ± 7.6 | 82.4 ± 9.8 |
| Artery | 85.5 ± 14.1 | 85.5 ± 7.9 | 85.3 ± 7.7 |
| Vein | 68.5 ± 8.0 | 62.8 ± 8.0 | 65.2 ± 8.0 |
| Artery-Vein | 17.2 ± 11.5 | 22.8 ± 12.5 | 20.7 ± 8.0 |

TABLE 2

|  |  | p | r |
|---|---|---|---|
| Mean of TD of Area a and Inferotemporal OS | HT | 0.0179 | 0.377 |
|  | LT | 0.6478 | 0.134 |
| Mean of TD of Area b and Superotemporal OS | HT | 0.6786 | 0.067 |
|  | LT | 0.9468 | 0.019 |
| MD and Average OS | HT | 0.1569 | 0.225 |
|  | LT | 0.6277 | 0.136 |
| MD and Average of Infertotemporal and Superotemporal OS | HT | 0.0374 | 0.334 |
|  | LT | 0.9783 | 0.030 |

It has been shown that prophylactic treatment of many diseases can maintain health for a long time, and at times manifestation of the disease can be prevented completely. In addition certain diseases such as glaucoma, degenerative retinal, optic nerve disorders and cell degenerations are difficult to predict until the diseases have manifested and have caused irreversible damage. These eye diseases are in need of early diagnosis. The purpose of this invention is to provide means of uncovering the precesses that would have remained undetected by the standard test. In other words, the present embodiment relates to a stress test applied to these predisposed conditions so that the disease can be detected early and treated prophylactically.

In some embodiments described herein, a test along with oxymetry of the retina-choroid is used. In the current embodiment, an instrument is applied along with other standard examination units such as visual acuity, electroreinography and perimetry etc. In this embodiment, a condition of the eye is measured at various intervals. For example, the condition may be measured before the instrument is applied and/or pressure is applied to the eye to determine a first value, after pressure has been applied to determine a second value, and/or after a predetermined time to determine a third value and/or the rate of return to the first value. Each of the first, second and third values can be compared to one another.

Electroretinography may evaluate the electrical responses of retinal cells to a light stimulus. Electrodes are usually placed on the cornea and on the forehead. A standard light stimulus is used to initiate electrical activity of the retinal cells which is displayed showing the time course of the signal's amplitude (voltage) in microvolts or lower. Various stimuli can produce a more specific response from certain retinal cells such as flash or pattern, background light, the colors of the stimulus and background.

In a dark-adapted condition, a rod response may be primarily obtained and in a light adapted state the ERG may show the cone response. The ERG waves are a-wave (photoreceptor) and b-wave (bipolar, Muller cells etc). The pattern ERG reflects the activity of the ganglion cells.

Multifocal ERG records ERG or VER from stimulation of different retinal locations. Each visual field location is stimulated with a separate stimulus in a different sequence. Therefore the ERG and VER can be analyzed using mathematical algorithm. e.g. *Multifocal Electroretinogram (mfERG)* MfERGs were recorded with the VERIS™ Science 5.1.12 (EDI: Electro-Diagnostic Imaging, San Mateo, Calif.). The recordings are performed under ordinary room light with the pupil dilated maximally. The stimulus is displayed on a monochrome CRT with a P4 (white) phosphor. An array of 37 densely packed hexagons stimulates the central 40° of the visual field (stretch factor was 13.18). An m-sequence rate of 75/s and cycle of $2^{14}-1$ steps results in a recording time of 3'38" (net). The stimulus intensity is 2.67 cd·s/m$^2$. Responses are recorded with a Burian-Allen bipolar contact lens electrode. A Camera/Refractor™ (Electro-Diagnostic Imaging) is used for refraction and to monitor eye position and fixation stability during the recordings. The signals are amplified (100,000×), band-pas filtered (10-300 Hz at half-amplitude) and digitalized with a 1,200 Hz sampling frequency. Density-scaled [nV/deg$^2$] amplitudes between first negative and first positive peaks of the first-order kernel (K1) are analyzed.

Perimetry measures differential light sensitivity in the visual field and its boundaries of the retina while the subject's gaze is fixed. One can use either a manual technique or more sophisticated units to do perimetry or a kinetic perimetry. For detection of visual fields loss or more subtle changes in the visual field, one can perform a threshold perimetry that can be evaluated within days, weeks, months, etc. with an automated unit. This technology has been used for detection and follow up of the diseases of the brain, optic nerve and retinal diseases such as glaucoma or age related macular degeneration/degenerative retinal diseases.

Visual acuity testing is now a standard of every optometry of opthalmology office and the techniques are known. The visual acuity is affected in all diseases and affects the central retina macula, and/or the optic nerve. This includes degenerative, inflammatory vascular and inherited diseases and toxicity of medications. In one embodiment, the visual acuity is determined at one or a plurality of times. For example, the visual acuity can be determined before and/or after the test.

Until now this instruments has not been used as a predictive in office tests for evaluation of ocular diseases such as glaucoma or optic nerve.

The test is some embodiments discussed herein utilizes an instrument such as a suction cup to increase the intraocular pressure (5-25 mg Hg or more) for a short period of time (1-10 minutes or more). The ERG, Perimetry or Oxymetry can be performed before and after the rise in the intraocular pressure. In normal subjects the full recovery of visual function including, visual acuity, ERG or multifocal ERG and perimetry/visual evoked response or visual evoked potential occurs much faster than a diseased or an eye predisposed to the diseased condition. A group of age matched healthy volunteers have been tested by the above mentioned techniques to create a standard value for each test. A significant alteration between the normal values in the suspected or predisposed to disease eye and normal aged matched subjects is considered as pathological or predisposed to the pathology. In ERG this can manifest itself in delay in recovery of a and b waves of the ERG or other changes, in perimetry it presents as a delay in recovery of the visual field in boundaries or threshold of the examined retinal sensitivity, or delayed in recovery of the visual acuity compared to the normal subjects.

The instrument for elevating the intraocular pressure can be a suction cup, contact lens or a hollow tube to which suction is applied and transmitted to the eye. It can also be a unit that pushes or applies a predetermined pressure on the eye for a given period. For example, the instrument can be any instrument herein described for altering or changing the pressure in the eye. This instrument can be equipped with a pressure sensor, indication the intraocular pressure or one can measure the pressure with another independent unit before or during the evaluation. The methodology can be used by a person skilled in the art with any other means or modifications.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

What is claimed is:

1. A method of testing for an ocular disease in an eye, comprising; measuring a stimulus of the eye to receive a first value; placing an instrument adjacent the surface of the eye; changing the pressure in the eye using the instrument after said measuring the condition to receive a first value; measuring the stimulus of the eye, after said changing the pressure, to receive a second value; and comparing the first value to the second value.

2. A method according to claim 1, wherein
each of said measurings includes placing electrodes on the cornea and forehead of a patient, initiating electrical activity of the retinal cells, determining one of a cone response and a rod response.

3. A method according to claim 2, wherein
said initiating electrical activity includes using a light stimulus.

4. A method according to claim 2, wherein
the activity of the retinal cells is displayed illustrating the time course of an amplitude of a signal in microvolts.

5. A method according to claim 1, wherein
each of said measurings includes measuring a stimulus response of a plurality of visual field locations, each visual field location being stimulated with a separate stimulus.

6. A method according to claim 5, further comprising
monitoring eye position and fixation stability during each of said measurings.

7. A method according to claim 5, wherein
said comparing includes comparing density scaled amplitudes between first negative and first positive peaks of first order kernels.

8. A method according to claim 5, wherein
each of said measurings includes measuring the stimulus response of a plurality of densely packed hexagons disposed in the central 40° of the visual field.

9. A method according to claim 1, wherein
each of said measurings includes measuring differential light sensitivity in the visual field of the retina of the eye and boundaries of the of the visual field of the retina while the position of the eye is fixed.

10. A method according to claim 1, wherein
said instrument is one of a suction cup, a contact lens and a hollow tube.

11. A method according to claim 1, further comprising
measuring the condition of the eye to receive a third value after said measuring the condition of the eye to receive a second value; and
comparing the first, second and third values.

12. A method according to claim 11, further comprising
waiting a predetermined time before said measuring the condition of the eye to receive a third value.

13. A method according to claim 1, further comprising
determining the visual acuity before said placing an instrument and after said changing the pressure.

\* \* \* \* \*